United States Patent [19]
Maurer et al.

[11] 3,987,169
[45] Oct. 19, 1976

[54] S-[O-ALKYL-ISOUREIDO-CARBONYLMETHYL]-(THIONO) (DI)THIOLPHOSPHORIC(PHOSPHONIC) ACID ESTERS AND ESTER-AMIDES

[75] Inventors: Fritz Maurer, Wuppertal; Ingeborg Hammann, Cologne; Bernhard Homeyer, Opladen; Wilhelm Stendel, Wuppertal, all of Germany

[73] Assignee: Bayer Aktiengesellschaft, Leverkusen, Germany

[22] Filed: Sept. 18, 1975

[21] Appl. No.: 614,820

[30] Foreign Application Priority Data
Sept. 24, 1974 Germany............................ 2445555

[52] U.S. Cl................................ 424/211; 260/943
[51] Int. Cl.² ..................... A01N 9/36; C07F 9/165; C07F 9/24; C07F 9/40
[58] Field of Search ............ 260/943, 938; 424/211

[56] References Cited
UNITED STATES PATENTS

| | | | |
|---|---|---|---|
| 3,022,215 | 2/1962 | Schuler................................ | 424/212 |
| 3,752,871 | 8/1973 | Stolzer et al........................ | 260/938 |
| 3,940,457 | 2/1976 | Hoffmann et al................... | 260/943 |

FOREIGN PATENTS OR APPLICATIONS
590,103   4/1960   Belgium

*Primary Examiner*—Richard L. Raymond
*Attorney, Agent, or Firm*—Burgess, Dinklage & Sprung

[57] ABSTRACT

S-[O-Alkyl-isoureido-carbonylmethyl]-(thiono) (di)thiolphosphoric(phosphonic) acid esters and ester-amides of the formula

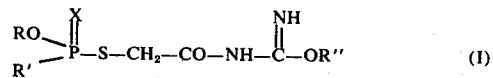

(I)

in which
R is alkyl with 1 to 6 carbon atoms or optionally halogen-substituted phenyl,
R' is alkyl with 1 to 4 carbon atoms, alkoxy with 1 to 4 carbon atoms, alkylthio with 1 to 6 carbon atoms, alkylamino with 1 to 6 carbon atoms, or phenyl,
R'' is alkyl with 1 to 6 carbon atoms, and X is oxygen or sulfur,
which possess insecticidal and acaricidal properties.

9 Claims, No Drawings

S-[O-ALKYL-ISOUREIDO-CARBONYLMETHYL]-(THIONO)(DI)THIOLPHOSPHORIC(PHOSPHONIC) ACID ESTERS AND ESTER-AMIDES

The present invention relates to and has for its objects the provision of particular new S-[O-alkyl-isoureido-carbonylmethyl]-(di)thiolphosphoric (phosphonic) acid esters and ester-amides, i.e. O,O-dialkyl- or O-alkyl-O-phenyl-S-[O-alkyl-isoureido-carbonylmethyl]-thiolphosphoric acid esters, O,S-dialkyl ester counterparts, phosphonic acid ester counterparts, O-alkyl or phenyl ester amide counterparts, and/or thiono counterparts, which possess insecticidal and acaricidal properties, active compositions in the form of mixtures of such compounds with solid and liquid dispersible carrier vehicles, and methods for producing such compounds and for using such compounds in a new way especially for combating pests, e.g. insects, and acarids, with other and further objects becoming apparent from a study of the within specification and accompanying examples.

It is known from German Published Specification DAS 1,173,889 and Belgian Patent Specification 590,103 that S-[carbalkoxycarbamoylmethyl]-(thiono)thiolphosphoric acid esters, for example O,O-diethyl-S-[N-methyl-N-carbethoxycarbamoylmethyl]-thiol-(Compound A) and O,O-diethyl-S-[N-carbethoxycarbamoylmethyl]-thiolthiono-phosphoric acid ester (Compound B), possess insecticidal and acaricidal properties.

The present invention provides, as new compounds, the S-[isoureido-carbonylmethyl]-(thiono)(di)thiolphosphoric (phosphonic) acid esters and ester-amides of the general formula

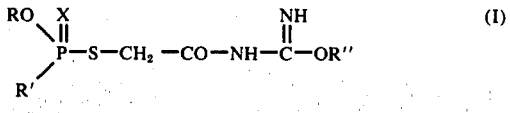

in which
R is alkyl with 1 to 6 carbon atoms or optionally halogen-substituted phenyl,
R' is alkyl with 1 to 4 carbon atoms, alkoxy with 1 to 4 carbon atoms, alkylthio with 1 to 6 carbon atoms, alkylamino with 1 to 6 carbon atoms, or phenyl,
R'' is alkyl with 1 to 6 carbon atoms, and X is oxygen or sulfur.

Preferably, R is straight-chain or branched alkyl with 1 to 5 (especially 1 to 4) carbon atoms, phenyl or phenyl monosubstituted or polysubstituted by chlorine, R' is straight-chain or branched alkyl or alkoxy with 1 to 3 (especially 1 or 2) carbon atoms, straight-chain or branched alkylthio with 1 to 5 (especially 1 to 4) carbon atoms or monoalkylamino with 1 to 5 (especially 1 to 4) carbon atoms, or phenyl, and R'' is straight-chain or branched alkyl with 1 to 5 (especially 1 to 4) carbon atoms.

Surprisingly, the S-[isoureido-carbonylmethyl]-(thiono) (di)thiolphosphoric(phosphonic) acid esters and ester-amides according to the invention possess a better insecticidal, including soil-insecticidal, and acaricidal action than the nearest compounds of analogous structure and of the same type of action known from the state of the art. The compounds according to the invention are active not only against insects and mites which damage plants but also against pests harmful to health and pests of stored products and, in the veterinary medicine filed, against ectoparasites, for example parasitic fly larvae. Accordingly, the compounds according to the invention represent a genuine enrichment of the art.

The invention also provides a process for the preparation of an S-[isoureido-carbonylmethyl]-(thiono)(-di)thiolphosphoric (phosphonic) acid ester or ester-amide of the general formula (I), in which a (thiono)(-di)thiolphosphoric(phosphonic) acid ester derivative or ester-amide derivative of the general formula

in which
R, R' and X have the above-mentioned meanings and
M is hydrogen or one equivalent of an alkali metal, alkaline earth metal or ammonium,
is reacted with an O-alkyl-N-halogenoacetyl-isourea of the general formula

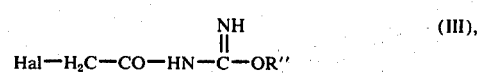

in which
R'' has the above-mentioned meaning and
Hal is halogen, preferably chlorine, if appropriate in the presence of an acid acceptor and if appropriate in the presence of a solvent or diluent.

If, for example, the potassium salt of O-ethyl-N-sec.-butyl-thionothiolphosphoric acid ester-amide and O-n-butyl-N-chloroacetylisourea are used as starting materials, the course of the reaction can be represented by the following equation:

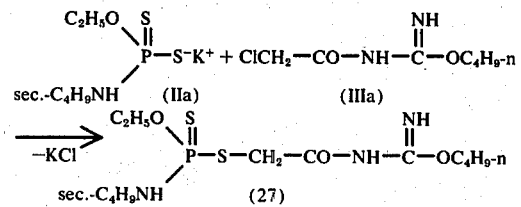

The (thiono)(di)thiolphosphoric(phosphonic) acid ester derivatives and ester-amide derivatives (II) to be used as starting materials are known from the literature and can be prepared according to generally customary processes (see, for example, German Published Specification DAS 1,141,634 and 1,164,408), as are the O-alkyl-N-halogenoacetylisoureas, which can be prepared, for example, from O-alkylisourea (see Houben-Weyl "Methoden der organischen Chemie" ("Methods of Organic Chemistry"), volume 8, page 170) and chloroacetyl chloride.

The following may be mentioned as examples of (thiono) (di)thiolphosphoric(phosphonic) acid ester derivatives and ester-amide derivatives (II) to be used in accordance with the process: O,O-dimethyl-, O,O-diethyl-, O,O-di-n-propyl-, O,O-di-isopropyl-, O,O-di-n-butyl-, O,O-di-isobutyl-, O,O-di-sec.-butyl-, O,O-di-tert.-butyl-, O-ethyl-O-n-propyl-, O-ethyl-O-isopropyl-, O-n-butyl-O-ethyl-, O-ethyl-O-sec.-butyl-, O-ethyl-O-methyl-, O-n-pentyl-O-methyl-, O-n-pentyl-O-ethyl-, O-n-pentyl-O-n-propyl-, O-n-pentyl-O-isopropyl-, O-methyl-O-phenyl-, O-ethyl-O-phenyl-, O-n-propyl-O-phenyl-, O-isopropyl-O-phenyl-, O-methyl-O-(2,4-dichlorophenyl)-, O-ethyl-O-(2,4-dichlorophenyl)-, O-n-propyl-O-(2,4-dichlorophenyl)-, O-isopropyl-O-(2,4-dichlorophenyl)-, O-methyl-O-(2-chlorophenyl)-, O-ethyl-O-(2-chlorophenyl)-, O-n-propyl-O-(2-chlorophenyl)-, O-isopropyl-O-(2-chlorophenyl)-, O-methyl-O-(3-chlorophenyl)-, O-ethyl-O-(3-chloropenyl)-, O-n-propyl-O-(3-chlorophenyl)-, O-isopropyl-O-(3-chlorophenyl)-, O-methyl-O-(4-chlorophenyl)-, O-ethyl-O-(4-chlorophenyl)-, O-n-propyl-O-(4-chlorophenyl)-, O-isopropyl-O-(4-chlorophenyl)-, O-methyl-O-(2,6-dichlorophenyl)-, O-ethyl-O-(2,6-dichlorophenyl)-, O-n-propyl-O-(2,6-dichlorophenyl)-, O-isopropyl-O-(2,6-dichlorophenyl)-, O-methyl-O-(2,4,5-trichlorophenyl)-, O-ethyl-O-(2,4,5-trichlorophenyl)-, O-n-propyl-O-(2,4,5-tri-chlorophenyl)-, O-isopropyl-O-(2,4,5-trichlorophenyl)-, O-methyl-O-pentachlorophenyl-, O-ethyl-O-pentachlorophenyl-, O-n-propyl-O-pentachlorophenyl- and O-isopropyl-O-penta-chlorophenyl-thiolophosphoric acid diesters, the corresponding alkali metal salts, alkaline earth metal salts or ammonium salts and, in each case, the thiono analogues; O,S-dimethyl-, O,S-diethyl-, O,S-di-n-propyl-, O,S-di-isopropyl-, O,S-di-n-butyl-, O,S-di-sec.-butyl-, O,S-di-isobutyl-, O,S-di-tert.-butyl-, O,S-di-pentyl-, O-ethyl-S-n-propyl-, O-n-propyl-S-ethyl-, O-iso-propyl-S-ethyl-, S-methyl-O-phenyl-, S-ethyl-O-phenyl-, S-n-propyl-O-phenyl-, S-isopropyl-O-phenyl-, S-ethyl-O-(2,4-dichlorophenyl)-, S-n-propyl-O-(2,4,5-trichlorophenyl)-and S-isopropyl-O-(2,4,5-trichlorophenyl)-dithiophosphoric acid diesters, the corresponding alkali metal salts, alkaline earth metal salts and ammonium salts, and in each case, the corresponding thiono analogues; O-methyl-, O-ethyl-, O-n-propyl-, O-isopropyl-, O-n-butyl-, O-isopropyl-, O-n-butyl-, O-isobutyl-, O-sec.-butyl-, O-tert.-butyl-, O-pentyl-, O-phenyl-, O-(2,4-dichlorophenyl)- and O-(2,4,5-trichloro-phenyl)-methane-, ethane-, n-propane-, isopropane- and benzene-thiolphosphonic acid esters, the corresponding alkali metal salts, alkaline earth meta salts and ammonium salts and, in each case, the corresponding thiono analogues; and O-methyl-N-methyl-, O-ethyl-N-methyl-, O-n-propyl-N-methyl-, O-isopropyl-N-methyl-, O-n-butyl-N-methyl-, O-sec.-butyl-N-methyl-, O-methyl-N-ethyl-, O-ethyl-N-ethyl-, O-n-propyl-N-ethyl-, O-isopropyl-N-ethyl-, O-n-butyl-N-ethyl-, O-sec.-butyl-N-ethyl-, O-methyl-N-n-propyl, O-ethyl-N-n-propyl-, O-n-propyl-N-n-propyl-, O-n-propyl-N-n-butyl-, O-isopropyl-N-ethyl-, O-isopropyl-N-n-butyl-, O-pentyl-N-ethyl-, O-pentyl-N-n-propyl-, O-isopropyl-N-sec.-butyl-, O-isopropyl-N-tert.-butyl- and O-isopropyl-N-pentyl-thiolphosphoric acid ester amides, the corresponding alkali metal salts, alkaline earth metal salts and ammonium salts and, in each case, the corresponding thiono analogues.

The following may be mentioned as examples of O-alkyl-N-halogenoacetyl-isoureas (III) to be reacted in accordance with the process: O-methyl-, O-ethyl-, O-n-propyl-, O-isopropyl-, O-n-butyl-, O-sec.-butyl-, O-isobutyl-, O-tert.-butyl- and O-n-pentyl-N-chloroacetyl-isoureas.

The process for the preparation of the compounds according to the invention is preferably carried out in the presence of suitable solvents and diluents. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly successful, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 0° and 100° C, preferably at from 35° to 40° C.

The reaction is in general allowed to take place under normal pressure.

To carry out the process, the starting materials are preferably employed in equimolar amounts. An excess of one or other component produces no significant advantages. The reaction is preferably carried out in one of the stated solvents, in most cases at an elevated temperature. After completion of the reaction, an organic solvent, for example toluene, is in general added to the reaction mixture, the phases are separated and the organic phase is worked up in the usual manner by washing, drying and distilling off the solvent.

The new compounds are frequently obtained in the form of oils which in most cases cannot be distilled without decomposition, but are freed from the last volatile constituents by so-called "slight distillation", that is to say by prolonged heating under reduced pressure to moderately elevated temperatures, and are purified in this way. They are characterised by the refractive index. Some of the compounds are obtained in the form of crystals of sharp melting point.

As already mentioned, the S-[isoureidocarbonylmethyl]-(thiono)(di)thiolphosphoric(phosphonic) acid esters and esteramides according to the invention are distinguished by an excellent insecticidal, including soil-insecticidal, and acaricidal activity. They are active not only against plant pests, pests harmful to health and pests of stored products, but also, in the veterinary medicine field, against animal parasites (ectoparasites), such as parasitic fly larvae. They couple a low phytotoxicity with a good action against both sucking and biting insects and against mites.

For this reason, the compounds according to the invention can be employed successfully as pesticides in plant protection and in the hygiene field, the field of protection of stored products and the veterinary field.

The economically important pests in agriculture and forestry, as well as pests of stored products, material pests and pests harmful to health, include: from the order of the Isopoda, for example, *Oniscus asellus*, *Armadillidium vulgare* and *Porcellio scaber*; from the order of the Diploda, for example, *Blaniulus guttulatus*; from the order of the Chilopoda, for example, *Geophilus carpophagus* and *Scutigera* spec.; from the order of the Symphyla, for example, *Scutigerella immaculata*; from the order of the Arachnida, for example, *Scorpio*

*maurus* and *Latrodectus mactans*; from the order of the Acarina, for example, *Acarus siro, Argas reflexus, Ornithodoros moubata, Dermanyssus gallinae, Eriophyes ribis, Phyllocoptruta oleivora, Boophilus microplus, Rhipicephalus evertsi, Sarcoptes scabiei,* Tarsonemus spec. *Bryobia praetiosa, Panonychus citri, Panonychus ulmi, Tetranychus tumidus* and *Tetranychus urticae*; from the order of the Thysanura, for example, *Lepisma saccharina*; from the order of the Collembola, for example, *Onychiurus armatus*; from the order of the Orthoptera, for example, *Blatta orientalis, Periplaneta americana, Leucophaea maderae, Blattella germanica, Acheta domesticus,* Gryllotalpa spec., *Locusta migratoria migratorioides, Melanoplus differentialis* and *Schistocerca gregaria*; from the order of the Dermaptera, for example, *Forficula auricularia*; from the order of the Isoptera, for example, *Reticulitermes* spec.; from the order of the Anoplura, for example, *Phylloxera vastatrix,* Pemphigus spec. and *Pediculus humanus corporis*; from the order of the Thysanoptera, for example, *Hercinothrips femoralis* and *Thrips tabaci*; from the order of the Heteroptera, for example, Eurygaster spec., *Dysdercus intermedius, Piesma quadrata, Cimex lectularius, Rhodnium prolixus* and Triatoma spec.; from the order of the Homoptera, for example, *Aleurodes brassicae, Bemisia tabaci, Trialeurodes vaporariorum, Aphis gossypii, Brevicoryne brassicae, Cryptomycus ribis, Doralis fabae, Doralis pomi, Eriosoma lanigerum, Hyalopterus arundinis, Macrosiphum, avenae, Myzus, cerasi, Myzus persicae, Phorodon humuli, Rhopalosiphum padi,* Empoasca spec., *Euscelis bilobatus, Nephotettix cincticeps, Lecanium corni, Saissetia oleae, Laodelphax striatellus, Nilaparvata lugens, Aonidiella aurantii, Aspidiotus, hederae, Pseudococcus* spec. and Psylla spec.; from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spec., *Buccalatrix thurberiella, Phyllocnistis citrella,* Agrotis spec., Euxoa spec., *Feltia* spec., *Earias insulana,* Heliothis spec., *Laphygma exigua, Mamestra brassicae, Panolis flammea, Prodenia litura,* Spodoptera spec., *Trichoplusia ni, Carpocapsa pomonella,* Pieris spec., Chilo spec., *Pyrausta nubilalis, Ephestia kühniella, Galleria mellonella, Cacoecia podana, Capua reticulana, Choristoneura fumiferana, Clysia ambiguella, Homona magnanima* and *Tortrix viridana;* from the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spec., *Psylliodes chrysocephala, Epilachna varivestis,* Atomaria spec., *Oryzaephilus surinamensis,* Anthonomus spec., Sitophilus spec., *Otiorrhynchus sulcatus, Cosmopolites sordidus, Ceuthorrhynchus assimilis, Hypera postica,* Dermestes spec., Trogoderma spec., Anthrenus spec., Attagenus spec., Lyctus spec., *Meligethes aeneus,* Ptinus spec., *Niptus hololeucus, Gibbium psylloides,* Tribolium spec., *Tenebrio molitor,* Agriotes spec., Conoderus spec., *Melolontha melolontha, Amphimallus solstitialis* and *Costelytra zealandica;* from the order of the Hymenoptera, for example, Diprion spec., Hoplocampa spec., Lasius spec., *Monomorium pharaonis* and Vespa spec.; from the order of the Diptera, for example, Aëdes spec., Anopheles spec., Culex spec., *Drosophila melanogaster, Musca domestica,* Fannia spec., *Stomoxys calcitrans,* Hypoderma spec., *Bibio hortulans, Oscinella frit,* Phormia spec., *Pegomyia hyoscyami, Calliphora erythrocephala,* Lucilia spec., Chrysomyia spec., *Ceratitis capitata, Dacus oleae* and *Tipula paludosa;* and from the order of the Siphonaptera, for example, *Xenopsylla cheopis.*

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides or nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to a most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following table:

Table 1

| Active compound | (*Plutella* test) | Active compound concentration in % | Degree of destruction in % after 3 days |
|---|---|---|---|
| $(C_2H_5O)_2\overset{S}{\underset{\|\|}{P}}-S-CH_2-\overset{O}{\underset{\|\|}{C}}-NH-\overset{O}{\underset{\|\|}{C}}-OC_2H_5$ (known) | (B) | 0.1 | 0 |
| $\begin{array}{c}C_2H_5\\ \diagdown\\ CH_3O\end{array}\overset{S}{\underset{\|\|}{P}}-S-CH_2-CO-NH-\overset{NH}{\underset{\|\|}{C}}-OCH_3$ | (8) | 0.1 | 100 |
| $\begin{array}{c}C_2H_5\\ \diagdown\\ CH_3O\end{array}\overset{S}{\underset{\|\|}{P}}-S-CH_2-CO-NH-\overset{NH}{\underset{\|\|}{C}}-OC_2H_5$ | (10) | 0.1 | 100 |
| $\begin{array}{c}C_2H_5\\ \diagdown\\ C_2H_5O\end{array}\overset{S}{\underset{\|\|}{P}}-S-CH_2-CO-NH-\overset{NH}{\underset{\|\|}{C}}-OCH_3$ | (1) | 0.1 | 100 |

Table 1-continued

| Active compound | (Plutella test) | Active compound concentration in % | Degree of destruction in % after 3 days |
|---|---|---|---|
| $\begin{array}{c}C_2H_5\\ \diagdown\\ C_2H_5O\end{array}\!\!\!\stackrel{S}{\underset{\|}{P}}\!\!-S-CH_2-CO-NH-\stackrel{NH}{\underset{\|}{C}}-OC_2H_5$ | (7) | 0.1 | 100 |
| $\begin{array}{c}C_2H_5\\ \diagdown\\ n\text{-}C_3H_7O\end{array}\!\!\!\stackrel{S}{\underset{\|}{P}}\!\!-S-CH_2-CO-NH-\stackrel{NH}{\underset{\|}{C}}-OCH_3$ | (6) | 0.1 | 100 |
| $\begin{array}{c}n\text{-}C_3H_7S\\ \diagdown\\ C_2H_5O\end{array}\!\!\!\stackrel{S}{\underset{\|}{P}}\!\!-S-CH_2-CO-NH-\stackrel{NH}{\underset{\|}{C}}-OCH_3$ | (19) | 0.1 | 100 |
| $\begin{array}{c}n\text{-}C_3H_7S\\ \diagdown\\ C_2H_5O\end{array}\!\!\!\stackrel{S}{\underset{\|}{P}}\!\!-S-CH_2-CO-NH-\stackrel{NH}{\underset{\|}{C}}-OC_3H_7\text{-iso}$ | (20) | 0.1 | 100 |

EXAMPLE 2

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (Brassica oleracea) which had been heavily infested with peach aphids (Myzus persicae) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 2

| Active compound | (Myzus test) | Active compound concentration in % | Degree of destruction in % after 1 day |
|---|---|---|---|
| $(C_2H_5O)_2\stackrel{S}{\underset{\|}{P}}-S-CH_2-\stackrel{O}{\underset{\|}{C}}-NH-\stackrel{O}{\underset{\|}{C}}-OC_2H_5$ (known) | (B) | 0.1<br>0.01<br>0.001 | 100<br>98<br>0 |
| $(C_2H_5O)_2\stackrel{S}{\underset{\|}{P}}-S-CH_2-\stackrel{O}{\underset{\|}{C}}-\underset{CH_3}{N}-\stackrel{O}{\underset{\|}{C}}-OC_2H_5$ (known) | (A) | 0.1<br>0.01<br>0.001 | 100<br>60<br>0 |
| $\begin{array}{c}C_2H_5\\ \diagdown\\ CH_3O\end{array}\!\!\!\stackrel{S}{\underset{\|}{P}}\!\!-S-CH_2-CO-NH-\stackrel{NH}{\underset{\|}{C}}-OC_3H_7\text{-}{iso}$ | (14) | 0.1<br>0.01<br>0.001 | 100<br>100<br>98 |
| $\begin{array}{c}C_2H_5\\ \diagdown\\ C_2H_5O\end{array}\!\!\!\stackrel{S}{\underset{\|}{P}}\!\!-S-CH_2-CO-NH-\stackrel{NH}{\underset{\|}{C}}-OCH_3$ | (1) | 0.1<br>0.01<br>0.001 | 100<br>100<br>99 |
| $\begin{array}{c}C_2H_5\\ \diagdown\\ C_2H_5O\end{array}\!\!\!\stackrel{S}{\underset{\|}{P}}\!\!-S-CH_2-CO-NH-\stackrel{NH}{\underset{\|}{C}}-OC_2H_5$ | (7) | 0.1<br>0.01<br>0.001 | 100<br>100<br>95 |
| $\begin{array}{c}C_2H_5\\ \diagdown\\ C_2H_5O\end{array}\!\!\!\stackrel{S}{\underset{\|}{P}}\!\!-S-CH_2-CO-NH-\stackrel{NH}{\underset{\|}{C}}-OC_3H_7\text{-}{iso}$ | (13) | 0.1<br>0.01<br>0.001 | 100<br>100<br>100 |
| $\begin{array}{c}C_2H_5\\ \diagdown\\ n\text{-}C_3H_7O\end{array}\!\!\!\stackrel{S}{\underset{\|}{P}}\!\!-S-CH_2-CO-NH-\stackrel{NH}{\underset{\|}{C}}-OCH_3$ | (6) | 0.1<br>0.01<br>0.001 | 100<br>100<br>90 |
| $\begin{array}{c}CH_3\\ \diagdown\\ \text{iso-}C_3H_7O\end{array}\!\!\!\stackrel{S}{\underset{\|}{P}}\!\!-S-CH_2-CO-NH-\stackrel{NH}{\underset{\|}{C}}-OC_2H_5$ | (12) | 0.1<br>0.01<br>0.001 | 100<br>100<br>100 |

Table 2-continued

| Active compound | (Myzus test) Active compound concentration in % | Degree of destruction in % after 1 day |
|---|---|---|
| $\begin{array}{c} CH_3 \diagdown \overset{S}{\underset{\|}{}} \\ \phantom{CH_3}\diagup P-S-CH_2-CO-NH-\overset{NH}{\underset{\|}{C}}-OC_3H_{7\text{-}iso} \\ iso\text{-}C_3H_7O \end{array}$ (15) | 0.1<br>0.01<br>0.001 | 100<br>100<br>98 |

EXAMPLE 3

Doralis test (systemic action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier, and the concentrate was diluted with water to the desired concentration.

Bean plants (*Vicia faba*) which had been heavily infested with bean aphid (*Doralis fabae*) were watered with the preparation of the active compound so that the preparation penetrated into the soil without wetting the leaves of the bean plants. The active compound was taken up from the soil by the bean plants and thus passed to the infested leaves.

After the specified perids of time, the degree of destruction was determined as a percentage. 100% means that all the aphids were killed; 0% means that none of the aphids were killed.

The active compounds, the concentrations of the active compounds, the evaluation times and the results can be seen from the following table:

Table 3

| Active compound | (Doralis test/systemic action) | Active compound concentration in % | Degree of destruction in % after 4 days |
|---|---|---|---|
| $(C_2H_5O)_2\overset{S}{\underset{\|}{P}}-S-CH_2-\overset{O}{\underset{\|}{C}}-\underset{\underset{CH_3}{\|}}{N}-\overset{O}{\underset{\|}{C}}-OC_2H_5$ (known) | (A) | 0.1 | 0 |
| $(CH_3O)_2\overset{S}{\underset{\|}{P}}-S-CH_2-CO-NH-\overset{NH}{\underset{\|}{C}}-OCH_3$ | (5) | 0.1 | 100 |
| $\begin{array}{c} C_2H_5\diagdown \overset{S}{\underset{\|}{}} \\ \phantom{C_2H_5}\diagup P-S-CH_2-CO-NH-\overset{NH}{\underset{\|}{C}}-OCH_3 \\ CH_3O \end{array}$ | (8) | 0.1 | 100 |
| $\begin{array}{c} C_2H_5\diagdown \overset{S}{\underset{\|}{}} \\ \phantom{C_2H_5}\diagup P-S-CH_2-CO-NH-\overset{NH}{\underset{\|}{C}}-OC_2H_5 \\ CH_3O \end{array}$ | (10) | 0.1 | 100 |
| $(C_2H_5O)_2\overset{S}{\underset{\|}{P}}-S-CH_2-CO-NH-\overset{NH}{\underset{\|}{C}}-OCH_3$ | (3) | 0.1 | 100 |
| $(C_2H_5O)_2\overset{O}{\underset{\|}{P}}-S-CH_2-CO-NH-\overset{NH}{\underset{\|}{C}}-OCH_3$ | (21) | 0.1 | 100 |
| $\begin{array}{c} C_2H_5\diagdown \overset{S}{\underset{\|}{}} \\ \phantom{C_2H_5}\diagup P-S-CH_2-CO-NH-\overset{NH}{\underset{\|}{C}}-OCH_3 \\ C_2H_5O \end{array}$ | (1) | 0.1 | 100 |
| $\begin{array}{c} C_2H_5\diagdown \overset{S}{\underset{\|}{}} \\ \phantom{C_2H_5}\diagup P-S-CH_2-CO-NH-\overset{NH}{\underset{\|}{C}}-OC_2H_5 \\ C_2H_5O \end{array}$ | (7) | 0.1 | 100 |
| $\begin{array}{c} C_2H_5\diagdown \overset{S}{\underset{\|}{}} \\ \phantom{C_2H_5}\diagup P-S-CH_2-CO-NH-\overset{NH}{\underset{\|}{C}}-OC_3H_{7\text{-}iso} \\ C_2H_5O \end{array}$ | (13) | 0.1 | 100 |
| $\begin{array}{c} C_2H_5\diagdown \overset{S}{\underset{\|}{}} \\ \phantom{C_2H_5}\diagup P-S-CH_2-CO-NH-\overset{NH}{\underset{\|}{C}}-OCH_3 \\ n\text{-}C_3H_7O \end{array}$ | (6) | 0.1 | 100 |
| $\begin{array}{c} CH_3\diagdown \overset{S}{\underset{\|}{}} \\ \phantom{CH_3}\diagup P-S-CH_2-CO-NH-\overset{NH}{\underset{\|}{C}}-OCH_3 \\ iso\text{-}C_3H_7O \end{array}$ | (11) | 0.1 | 100 |
| $\begin{array}{c} CH_3\diagdown \overset{S}{\underset{\|}{}} \\ \phantom{CH_3}\diagup P-S-CH_2-CO-NH-\overset{NH}{\underset{\|}{C}}-OC_2H_5 \\ iso\text{-}C_3H_7O \end{array}$ | (12) | 0.1 | 100 |

Table 3-continued (*Doralis* test/systemic action)

| Active compound | | Active compound concentration in % | Degree of destruction in % after 4 days |
|---|---|---|---|
| iso-$C_3H_7$—NH\\P(=S)(—S—$CH_2$—CO—NH—C(=NH)—$OCH_3$)/$C_2H_5O$ | (4) | 0.1 | 100 |

EXAMPLE 4

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following table:

Table 4

| Active compound | | Active compound concentration in % | Degree of destruction in % after 2 days |
|---|---|---|---|
| ($C_2H_5O)_2$P(=S)—S—$CH_2$—C(=O)—NH—C(=O)—$OC_2H_5$ (known) | (B) | 0.1 | 0 |
| $C_2H_5$\\P(=S)(—S—$CH_2$—CO—NH—C(=NH)—$OCH_3$)/$CH_3O$ | (8) | 0.1 | 95 |

EXAMPLE 5

Test with parasitic fly larvae
Solvent: 35 parts by weight of ethylene polyglycol monomethyl ether; 35 parts by weight of nonylphenol polyglycol ether To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (*Lucilia cuprina*) were introduced into a test tube which contained approx. 2 cm³ of horse muscle. 0.5 ml of the preparation of active compound was applied to this horse meat. After 24 hours, the degree of destruction in % was determined. 100% means that all the larvae had been killed and 0% means that no larvae had been killed.

The active compounds investigated, the concentrations of the active compounds used and the results obtained can be seen from the table which follows:

Table 5

| Active compound | | Active compound concentration in ppm | Degree of destruction in % |
|---|---|---|---|
| n-$C_3H_7S$\\P(=S)(—S—$CH_2$—CO—NH—C(=NH)—$OCH_3$)/$C_2H_5O$ | (19) | 100<br>30<br>10<br>3 | 100<br>100<br>100<br>0 |
| ($C_2H_5O)_2$P(=O)—S—$CH_2$—CO—NH—C(=NH)—$OCH_3$ | (21) | 100<br>30<br>10<br>3 | 100<br>100<br>50<br>0 |

EXAMPLE 6

Critical concentration test/soil insects
Test insect: Phorbia antiqua - grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectivenes is 100% if all test insects had been killed and is 0% if exactly as many test insects were still alive as in the case of the untreated control.

The active compounds, amounts used and results can be seen from the table which follows:

Table 6

Critical concentration test
(*Phorbia antiqua* — grubs in the soil)

| Active compound | | Degree of destruction at an active compound concentration of 10 ppm |
|---|---|---|
| $(C_2H_5O)\overset{S}{\underset{\parallel}{P}}-S-CH_2-\overset{O}{\underset{\parallel}{C}}-NH-\overset{O}{\underset{\parallel}{C}}-OC_2H_5$ (known) | (B) | 0 |
| $\begin{array}{c}C_2H_5\\ \\ n\text{-}C_3H_7O\end{array}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!$ | | |

The compounds (with results all = 100 at 10 ppm) listed are:

- (6) $\begin{array}{c}C_2H_5\\ n\text{-}C_3H_7O\end{array}\!\!\!\!P(=S)-S-CH_2-CO-NH-C(=NH)-OCH_3$ — 100
- (7) $\begin{array}{c}C_2H_5\\ C_2H_5O\end{array}\!\!\!\!P(=S)-S-CH_2-CO-NH-C(=NH)-OC_2H_5$ — 100
- (8) $\begin{array}{c}C_2H_5\\ CH_3O\end{array}\!\!\!\!P(=S)-S-CH_2-CO-NH-C(=NH)-OCH_3$ — 100
- (10) $\begin{array}{c}C_2H_5\\ CH_3O\end{array}\!\!\!\!P(=S)-S-CH_2-CO-NH-C(=NH)-OC_2H_5$ — 100
- (11) $\begin{array}{c}CH_3\\ iso\text{-}C_3H_7O\end{array}\!\!\!\!P(=S)-S-CH_2-CO-NH-C(=NH)-OCH_3$ — 100
- (12) $\begin{array}{c}CH_3\\ iso\text{-}C_3H_7O\end{array}\!\!\!\!P(=S)-S-CH_2-CO-NH-C(=NH)-OC_2H_5$ — 100
- (13) $\begin{array}{c}C_2H_5\\ C_2H_5O\end{array}\!\!\!\!P(=S)-S-CH_2-CO-NH-C(=NH)-OC_3H_7\text{-}iso$ — 100
- (14) $\begin{array}{c}C_2H_5\\ CH_3O\end{array}\!\!\!\!P(=S)-S-CH_2-CO-NH-C(=NH)-OC_3H_7\text{-}iso$ — 100
- (15) $\begin{array}{c}CH_3\\ iso\text{-}C_3H_7O\end{array}\!\!\!\!P(=S)-S-CH_2-CO-NH-C(=NH)-OC_3H_7\text{-}iso$ — 100
- (16) $(CH_3O)_2P(=S)-S-CH_2-CO-NH-C(=NH)-OC_3H_7\text{-}iso$ — 100
- (20) $\begin{array}{c}n\text{-}C_3H_7S\\ C_2H_5O\end{array}\!\!\!\!P(=S)-S-CH_2-CO-NH-C(=NH)-OC_3H_7\text{-}iso$ — 100
- (21) $(C_2H_5O)_2P(=O)-S-CH_2-CO-NH-C(=NH)-OCH_3$ — 100

The process of this invention is illustrated by the following preparative Examples.

EXAMPLE 7 a. The starting materials could be prepared, for example, as follows:

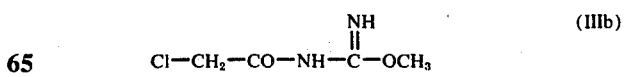

(IIIb)

56.5 g (0.5 mole) of chloroacetyl chloride were added dropwise at 20°–25° C to a mixture of 101 g (1 mole) of triethylamine, 55 g (0.5 mole) of O-methyl-isourea hydrochloride (Houben-Weyl, "Methoden der organischen Chemie" ("Methods of Organic Chemistry"), volume 8, page 170) and 300 ml of acetonitrile. The mixture was then stirred for a further 18 hours at room temperature and the salt which had precipitated was filtered off and rinsed with acetonitrile. The filtrate was concentrated in vacuo: 200 ml of water were added to the residue and the product was filtered off after crystallization. This gave 36.5 g (49% of theory) of N-chloroacetyl-O-methyl-isourea in the form of a grey powder of melting point 123° C.

The following could be prepared analogously:

| Formula | Yield (% of theory) | Melting point °C |
|---|---|---|
| $Cl-CH_2-CO-NH-\underset{\underset{NH}{\|\|}}{C}-OC_2H_5$ (IIIc) | 52 | 57 |
| $Cl-CH_2-CO-NH-\underset{\underset{NH}{\|\|}}{C}-OC_3H_{7\text{-}iso}$ (IIId) | 55 | 40 | b.

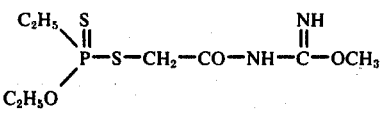

A mixture of 15.1 g (0.1 mole) of N-chloroacetyl-O-methyl-isourea, 20.8 g (0.1 mole) of the potassium salt of ethanedithiophosphonic acid O-ethyl ester and 300 ml of acetonitrile was stirred for 2 hours at 40°–50° C. 400 ml of toluene were then added to the reaction mixture and the latter was washed twice with 300 ml of water at a time. The organic phase was separated off, dried over sodium sulfate and freed from the solvent in vacuo. The residue was subjected to slight distillation. 23 g (81% of theory) of O-ethyl-S-[O-methylisoureidocarbonylmethyl]-thionothiol-ethanephosphonic acid ester were thus obtained in the form of a yellow oil having a refractive index $n_D^{25}$ of 1.5570.

The following compounds could be pepared analogously:

| Compound No. | Formula | Yield (% of theory) | Physical data (refractive index, melting point ° C) |
|---|---|---|---|
| (2) | $\underset{C_2H_5O}{\overset{C_6H_5}{\diagdown}}\overset{O}{\underset{\|\|}{P}}-S-CH_2-CO-NH-\underset{\underset{NH}{\|\|}}{C}-OC_3H_7\text{-}iso$ | 87 | $n_D^{23}: 1.5492$ |
| (3) | $(C_2H_5O)_2\overset{S}{\underset{\|\|}{P}}-S-CH_2-CO-NH-\underset{\underset{NH}{\|\|}}{C}-OCH_3$ | 62 | 35 |
| (4) | $\underset{C_2H_5O}{\overset{iso-C_3H_7-NH}{\diagdown}}\overset{S}{\underset{\|\|}{P}}-S-CH_2-CO-NH-\underset{\underset{NH}{\|\|}}{C}-OCH_3$ | 64 | 50 |
| (5) | $(CH_3O)_2\overset{S}{\underset{\|\|}{P}}-S-CH_2-CO-NH-\underset{\underset{NH}{\|\|}}{C}-OCH_3$ | 45 | 30 |
| (6) | $\underset{n\text{-}C_3H_7O}{\overset{C_2H_5}{\diagdown}}\overset{S}{\underset{\|\|}{P}}-S-CH_2-CO-NH-\underset{\underset{NH}{\|\|}}{C}-OCH_3$ | 57 | $n_D^{22}: 1.5467$ |
| (7) | $\underset{C_2H_5O}{\overset{C_2H_5}{\diagdown}}\overset{S}{\underset{\|\|}{P}}-S-CH_2-CO-NH-\underset{\underset{NH}{\|\|}}{C}-OC_2H_5$ | 67 | $n_D^{22}: 1.5553$ |
| (8) | $\underset{CH_3O}{\overset{C_2H_5}{\diagdown}}\overset{S}{\underset{\|\|}{P}}-S-CH_2-CO-NH-\underset{\underset{NH}{\|\|}}{C}-OCH_3$ | 42 | $n_D^{22}: 1.5612$ |
| (9) | $(CH_3O)_2\overset{S}{\underset{\|\|}{P}}-S-CH_2-CO-NH-\underset{\underset{NH}{\|\|}}{C}-OC_2H_5$ | 56 | $n_D^{22}: 1.5390$ |
| (10) | $\underset{CH_3O}{\overset{C_2H_5}{\diagdown}}\overset{S}{\underset{\|\|}{P}}-S-CH_2-CO-NH-\underset{\underset{NH}{\|\|}}{C}-OC_2H_5$ | 56 | $n_D^{22}: 1.5608$ |
| (11) | $\underset{iso\text{-}C_3H_7O}{\overset{CH_3}{\diagdown}}\overset{S}{\underset{\|\|}{P}}-S-CH_2-CO-NH-\underset{\underset{NH}{\|\|}}{C}-OCH_3$ | 53 | $n_D^{22}: 1.5495$ |
| (12) | $\underset{iso\text{-}C_3H_7O}{\overset{CH_3}{\diagdown}}\overset{S}{\underset{\|\|}{P}}-S-CH_2-CO-NH-\underset{\underset{NH}{\|\|}}{C}-OC_2H_5$ | 69 | $n_D^{22}: 1.5505$ |

-continued

| Compound No. | Formula | Yield (% of theory) | Physical data (refractive index, melting point °C) |
|---|---|---|---|
| (13) | (C$_2$H$_5$)(C$_2$H$_5$O)P(=S)–S–CH$_2$–CO–NH–C(=NH)–OC$_3$H$_7$-iso | 73 | $n_D^{22}$: 1.5443 |
| (14) | (C$_2$H$_5$)(CH$_3$O)P(=S)–S–CH$_2$–CO–NH–C(=NH)–OC$_3$H$_7$-iso | 57 | $n_D^{22}$: 1.5516 |
| (15) | (CH$_3$)(iso-C$_3$H$_7$O)P(=S)–S–CH$_2$–CO–NH–C(=NH)–OC$_3$H$_7$iso | 68 | $n_D^{22}$: 1.5380 |
| (16) | (CH$_3$O)$_2$P(=S)–S–CH$_2$–CO–NH–C(=NH)–OC$_3$H$_7$-iso | 63 | $n_D^{23}$: 1.5273 |
| (17) | (CH$_3$)(2,4-Cl$_2$C$_6$H$_3$O)P(=S)–S–CH$_2$–CO–NH–C(=NH)–OCH$_3$ | 51 | $n_D^{23}$: 1.6023 |
| (18) | (CH$_3$)(2,4-Cl$_2$C$_6$H$_3$O)P(=S)–S–CH$_2$–CO–NH–C(=NH)–OC$_3$H$_7$-iso | 45 | $n_D^{23}$: 1.5850 |
| (19) | (n-C$_3$H$_7$S)(C$_2$H$_5$O)P(=S)–S–CH$_2$–CO–NH–C(=NH)–OCH$_3$ | 66 | $n_D^{23}$: 1.5629 |
| (20) | (n-C$_3$H$_7$S)(C$_2$H$_5$O)P(=S)–S–CH$_2$–CO–NH–C(=NH)–OC$_3$H$_7$-iso | 69 | $n_D^{23}$: 1.5405 |
| (21) | (C$_2$H$_5$O)$_2$P(=O)–S–CH$_2$–CO–NH–C(=NH)–OCH$_3$ | 88 | $n_D^{23}$: 1.5042 |
| (22) | (C$_6$H$_5$)(C$_2$H$_5$O)P(=S)–S–CH$_2$–CO–NH–C(=NH)–OC$_3$H$_7$-iso | 69 | $n_D^{23}$: 1.5703 |

Other compounds which can be similarly prepared include:

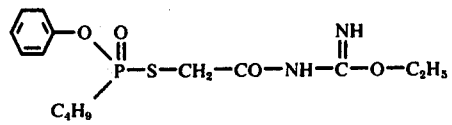

(23) (C$_6$H$_5$O)(C$_4$H$_9$)P(=O)–S–CH$_2$–CO–NH–C(=NH)–O–C$_2$H$_5$

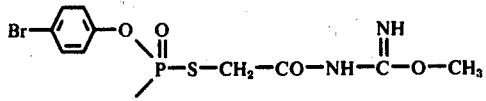

(24) (4-Br-C$_6$H$_4$O)(C$_4$H$_9$O)P(=O)–S–CH$_2$–CO–NH–C(=NH)–O–CH$_3$

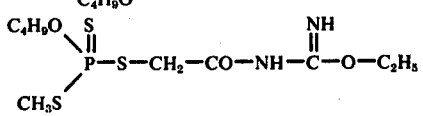

(25) (C$_4$H$_9$O)(CH$_3$S)P(=S)–S–CH$_2$–CO–NH–C(=NH)–O–C$_2$H$_5$

-continued

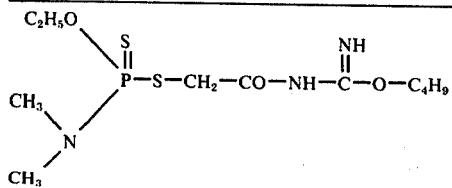
(26)

and the like.

It will be appreciated that the instant specification and examples are set forth by way of illustration and not limitation, and that various modifications and changes may be made without departing from the spirit and scope of the present invention.

What is claimed is:

1. An S-[isoureido-carbonylmethyl]-(thiono)(di)thiolphosphoric(phosphonic) acid ester or ester-amide of the formula

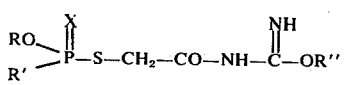

in which
R is alkyl with 1 to 6 carbon atoms or optionally halogen-substituted phenyl,
R' is alkyl with 1 to 4 carbon atoms, alkoxy with 1 to 4 carbon atoms, alkylthio with 1 to 6 carbon atoms, alkylamino with 1 to 6 carbon atoms, or phenyl,
R" is alkyl with 1 to 6 carbon atoms, and
X is oxygen or sulfur.

2. A compound according to claim 1, in which R is alkyl with 1 to 5 carbon atoms, phenyl or chlorophenyl, R' is alkyl or alkoxy each with 1 to 3 carbon atoms, alkylthio with 1 to 5 carbon atoms, monoalkyl-amino with 1 to 5 carbon atoms, or phenyl, and R" is alkyl with 1 to 5 carbon atoms.

3. The compound according to claim 1 wherein such compound is O-ethyl-S-[O-methylisoureidocarbonyl-methyl]-thionothiol-ethanephosphonic acid ester of the formula

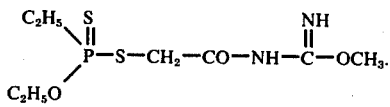

4. The compound according to claim 1 wherein such compound is O-n-propyl-S-[O-methylisoureidocarbonyl-methyl]-thionothiol-ethanephosphonic acid ester of the formula

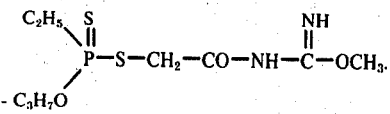

5. The compound according to claim 1 wherein such compound is O-isopropyl-S-[O-methylisoureidocarbonyl-methyl]-thionothiol-methanephosphonic acid ester of the formula

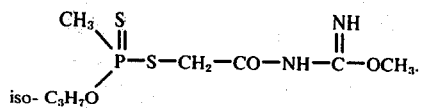

6. The compound according to claim 1 wherein such compound is O-isopropyl-S-[O-ethylisoureidocarbonyl-methyl]-thionothiol-methanephosphonic acid ester of the formula

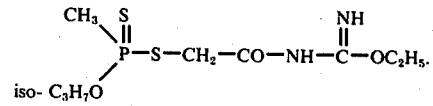

7. An insecticidal or acaricidal composition containing as active ingredient an insecticidally or acaricidally effective amount of a compound according to claim 1 in admixture with a diluent.

8. A method of combating insects or acarids which comprises applying to the insects or acarids or to a habitat thereof an insecticidally or acaricidally effective amount of a compound according to claim 1.

9. The method according to claim 8 in which said compound is
O-ethyl-S-[O-methylisoureidocarbonylmethyl]-thionothiol-ethanephosphonic acid ester,
O-n-propyl-S-[O-methylisoureidocarbonylmethyl]-thionothiol-ethanephosphonic acid ester,
O-isopropyl-S-[O-methylisoureidocarbonylmethyl]-thionothiol-methanephosphonic acid ester, or
O-isopropyl-S-[O-ethylisoureidocarbonylmethyl]-thionothiol-methanephosphonic acid ester.

* * * * *